(12) United States Patent
De Beer (10) Patent No.: US 11,091,670 B2
(45) Date of Patent: Aug. 17, 2021

(54) METHOD FOR CONNECTING TWO OBJECTS USING A POLYMER COMPOSITION AND A SYSTEM, FOR USE IN A COSMETIC PROCEDURE

(71) Applicant: TSK Laboratory Europe B.V., Oisterwijk (NL)

(72) Inventor: Isodoris Angelinus Quirinus Maria De Beer, Oisterwijk (NL)

(73) Assignee: TSK Laboratory Europe B.V., Oisterwijk (NL)

( * ) Notice: Subject to any disclaimer, the term of this patent is extended or adjusted under 35 U.S.C. 154(b) by 420 days.

(21) Appl. No.: 15/773,311

(22) PCT Filed: Nov. 7, 2016

(86) PCT No.: PCT/NL2016/050773
§ 371 (c)(1),
(2) Date: May 3, 2018

(87) PCT Pub. No.: WO2017/078532
PCT Pub. Date: May 11, 2017

(65) Prior Publication Data
US 2018/0320026 A1 Nov. 8, 2018

(30) Foreign Application Priority Data
Nov. 5, 2015 (EP) .................................... 15193253

(51) Int. Cl.
*C09J 5/00* (2006.01)
*A61M 5/34* (2006.01)
(Continued)

(52) U.S. Cl.
CPC .................. *C09J 5/00* (2013.01); *A61K 8/66* (2013.01); *A61K 38/4893* (2013.01);
(Continued)

(58) Field of Classification Search
CPC ...... B29C 2035/0827; B29C 2035/085; B29C 65/1406; C09J 5/00; A61M 5/343; A61M 5/349
See application file for complete search history.

(56) References Cited

U.S. PATENT DOCUMENTS 4,581,024 A * 4/1986 Swenson ............... A61M 5/343
604/240
4,776,849 A * 10/1988 Shinno .............. A61M 25/0014
604/533

(Continued)

FOREIGN PATENT DOCUMENTS

CN 103198841 A 7/2013
DE 10252838 A1 6/2004
(Continued)

OTHER PUBLICATIONS

Mar. 29, 2012—Meyer, Nora "Merkblatt: injizierbare Produkte zur Faltenbehandlung in Kosmetikstudios" XP055283945 pp. 1-5.
Feb. 2, 2017—ISR and Written Opinion PCT/NL2016/050773.

*Primary Examiner* — Daniel McNally
(74) *Attorney, Agent, or Firm* — Banner & Witcott, Ltd.

(57) ABSTRACT

The invention is directed to a method for using a polymer composition for connecting a first object to a second object, wherein the method comprises, the step of applying a polymer composition to at least part of the surface of at least one of the first object or second object; connecting the first object and the second object at the surface where the polymer composition is applied and irradiating the polymer composition using UV-radiation over a first time period, obtaining a UV radiated polymer composition; irradiating the UV radiated polymer composition with gamma-radiation over a second time period obtaining a gamma radiated polymer. The invention also relates to a system of a plastic object and a metal object connected by the method of the (Continued)

invention. In addition, the invention relates to a cosmetic method for anti-aging skin treatment wherein the method comprises the steps of: subcutaneously administering of an effective amount a of a dermal filler or *Botulinum* toxin to an area of skin, preferably the face and/or neck area, wherein the administering is performed by a syringe and a hypodermic needle or cannula of the invention.

9 Claims, 2 Drawing Sheets

(51) Int. Cl.

| | |
|---|---|
| *C09J 133/06* | (2006.01) |
| *B29C 65/14* | (2006.01) |
| *A61K 8/66* | (2006.01) |
| *A61K 38/48* | (2006.01) |
| *A61L 27/00* | (2006.01) |
| *A61Q 19/08* | (2006.01) |
| *C09J 175/16* | (2006.01) |
| *B29C 35/08* | (2006.01) |

(52) U.S. Cl.

CPC ............. *A61L 27/00* (2013.01); *A61M 5/343* (2013.01); *A61M 5/349* (2013.01); *A61Q 19/08* (2013.01); *B29C 65/1406* (2013.01); *C09J 133/06* (2013.01); *C12Y 304/24069* (2013.01); *A61M 2207/00* (2013.01); *A61M 2210/04* (2013.01); *B29C 2035/085* (2013.01); *B29C 2035/0827* (2013.01); *C09J 175/16* (2013.01); *C09J 2301/416* (2020.08); *C09J 2400/163* (2013.01); *C09J 2400/226* (2013.01); *C09J 2433/00* (2013.01); *C09J 2467/006* (2013.01); *C09J 2475/00* (2013.01)

(56) References Cited

U.S. PATENT DOCUMENTS

| | | | | |
|---|---|---|---|---|
| 6,129,710 | A | 10/2000 | Padgett et al. | |
| 6,187,400 | B1 * | 2/2001 | Woo | A61L 29/041 428/36.6 |
| 6,299,596 | B1 | 10/2001 | Ding | |
| 7,967,796 | B2 | 6/2011 | Sakurai et al. | |
| 9,073,296 | B2 | 7/2015 | Fäcke et al. | |
| 2004/0049163 | A1 * | 3/2004 | Murashita | A61M 5/3273 604/263 |
| 2007/0079838 | A1 | 4/2007 | Seckel | |
| 2013/0196944 | A1 | 8/2013 | Barg | |
| 2013/0277824 | A1 * | 10/2013 | Mahler | H01L 24/30 257/734 |
| 2014/0069581 | A1 * | 3/2014 | Ogawa | G02B 1/14 156/275.5 |
| 2014/0166202 | A1 * | 6/2014 | Fathi | C09J 5/04 156/272.2 |

FOREIGN PATENT DOCUMENTS

| | | | |
|---|---|---|---|
| EP | 0290147 | A2 | 11/1988 |
| JP | 60126166 | | 7/1985 |
| JP | 2001524013 | | 11/2001 |
| JP | 2002524597 | | 8/2002 |
| WO | 9851358 | A1 | 11/1998 |
| WO | 0014146 | A1 | 9/1999 |
| WO | 2008072229 | A2 | 6/2008 |
| WO | 2012052562 | A1 | 4/2012 |
| WO | 2013028904 | A2 | 2/2013 |
| WO | 2015011204 | A1 | 1/2015 |
| WO | 2015/144863 | A1 | 10/2015 |

* cited by examiner

METHOD FOR CONNECTING TWO OBJECTS USING A POLYMER COMPOSITION AND A SYSTEM, FOR USE IN A COSMETIC PROCEDURE

CROSS-REFERENCE TO RELATED APPLICATIONS

This application is a U.S. National Stage application under 35 U.S.C. § 371 of International Application PCT/NL2016/050773 (published as WO 2017/078532 A1), filed Nov. 7, 2016 which claims the benefit of priority to Application EP 15193253.0, filed Nov. 5, 2015. Benefit of the filing date of each of these prior applications is hereby claimed. Each of these prior applications is hereby incorporated by reference in its entirety.

The invention relates to a method for forming a system by two objects using a polymer composition.

In U.S. Pat. No. 7,967,796, an adhesive compound is described for joining needle-members to hubs or a needle-base members to form an injection needle. Such hubs are commonly made from polypropylene. In U.S. Pat. No. 7,967,796 an aliphatic epoxy resin is used. Needles may be used for injection of dermal fillers which have a high viscosity and may contain particles that make the injection more difficult. For example, collagen gel is a known dermal filler and has a high viscosity and may be as high as $6.6 \cdot 10^4$ Pa·s. Often dermal fillers such as collagen are many times more viscous than water, even as much as $10^8$ times more viscous than water. The viscous dermal filler also has a high drag, and may have an interphase drag coefficient as high as $6.4 \cdot 10^9$ Pa·s·m$^2$. The injection of dermal fillers requires high injection pressure to overcome drag forces associated with injection. These forces put extra strain on the needle or cannula and raises a risk of structural failure of the injection needle or cannula, such as leakage and pop-off. The dermal filler is often injected manually while the needle or cannula is inserted in the skin. Leakage, breaking, pop-off from the needle or cannula while injected in the skin may result in serious injury.

Accordingly, a need is felt for reliably connecting two objects, in particular a plastic object and a metal object, more in particular a needle hub and a needle or cannula to form an injection needle, with a polymer composition while preventing or at least substantially reducing the risk of breaking, leakage and/or pop-off of the confronting surfaces of the two objects. In particular, the connection should be strong enough to allow an injection needle to perform injection of viscous material. Additionally, a need is felt to provide an injection needle or cannula which complies with medical legislation.

Accordingly, it is an object of the invention to provide a method to connect two objects to each other. Another object is to provide a system of two objects, for example a metal object and a plastic object that are connected. Preferably, at least one of the disadvantages of the prior art is reduced or overcome. It is further also an object of the invention to provide a method for producing a needle or cannula suitable for dermal filler injection. Preferably the method to produce the hypodermic needle or cannula is more efficient in assembly and/or operation.

To this end the invention provides a method, and a system wherein a first object and a second object are connected by using a polymer composition, wherein the polymer composition is irradiated with UV light and with gamma radiation. Surprisingly it was found that the gamma radiation provides for a stronger connection between the two objects.

SUMMARY OF THE INVENTION

In a first aspect the invention is directed to a method for using a polymer composition for connecting a first object to a second object, wherein the method comprises:

applying a polymer composition to at least part of the surface of at least one of the first object or second object;

connecting the first object and the second object at the surface where the polymer composition is applied and irradiating the polymer composition using UV-radiation over a first time period, obtaining a UV radiated polymer composition;

irradiating the UV radiated polymer composition with gamma-radiation over a second time period obtaining a gamma radiated polymer.

Optionally, the first object comprises plastic or metal. Optionally the first object is substantially in its entirety made of plastic or metal. Optionally the first object comprises for more than 50 wt % of plastic or metal. Optionally the first object comprises for more than 60 wt % of plastic or metal. Optionally the first object comprises for more than 70 wt % of plastic or metal. Optionally the first object comprises for more than 80 wt % of plastic or metal. Optionally the first object comprises for more than 90 wt % of plastic or metal. Optionally the first object comprises for more than 95 wt % of plastic or metal.

Optionally the second object comprises plastic or metal. Optionally the second object is substantially in its entirety made of plastic or metal. Optionally the second object comprises for more than 50 wt % of plastic or metal. Optionally the second object comprises for more than 60 wt % of plastic or metal. Optionally the second object comprises for more than 70 wt % of plastic or metal. Optionally the second object comprises for more than 80 wt % of plastic or metal. Optionally the second object comprises for more than 90 wt % of plastic or metal. Optionally the second object comprises for more than 95 wt % of plastic or metal.

Optionally the first and second object are of a different material, preferably one object is a metal object and the other object is a plastic object. Optionally the first object comprises metal and the second object comprises plastic. Optionally the first object comprises plastic and the second object comprises metal.

Optionally the first and/or second object has a surface to volume ratio of 0.005 mm$^2$/mm$^3$-40 mm$^2$/mm$^3$. Optionally the first and/or second object has a surface to volume ratio of 0.2 mm$^2$/mm$^3$-27 mm$^2$/mm$^3$. Optionally the first and/or second object has a surface to volume ratio of 2.5 mm$^2$/mm$^3$-13.5 mm$^2$/mm$^3$. For hollow cylindrical objects, such as needles with an inner and outer diameter, it will be appreciated that the volume and surface is based on the outer diameter, or outer dimensions of the object. Optionally at least one of the first or second object has a cylindrical shape. Optionally at least one of the first or second object is open ended. Optionally at least one of the first or second object has a hollow cylindrical shape. Optionally at least one of the first or second object has a slanted tip. For a needle a slanted tip eases the penetration of the skin.

Optionally the second time period provides a gamma-radiation dosage of between 5 and 80 kGy. Optionally the second time period provides a gamma-radiation dosage of between 25 and 50 kGy. Optionally the second time period or the gamma-radiation dosage provides a sterility assurance level, of at least 2 log reduction for micro-organisms for the first object and the second object. Optionally the second time period or the gamma-radiation dosage provides a sterility assurance level, of at least 2-12 log reduction for microorganisms for the first object and the second object. Optionally the second time period or the gamma-radiation dosage provides a sterility assurance level, of at least 3-10 log reduction for micro-organisms for the first object and the second object. Optionally the second time period or the gamma-radiation dosage provides a sterility assurance level, of at least 4-9 log reduction for micro-organisms for the first object and the second object. Optionally the second time period or the gamma-radiation dosage provides a sterility assurance level, of at least 5-8 log reduction for micro-organisms for the first object and the second object. Optionally the second time period or the gamma-radiation dosage provides a sterility assurance level, of at least 6-7 log reduction for micro-organisms for the first object and the second object.

Optionally the polymer composition is provided substantially free of solvents that are capable of a chemical reaction during UV radiation and/or gamma radiation.

Optionally the polymer composition is curable under the influence of visible light or UV light, or both. Optionally the polymer composition is fluorescent. Optionally the polymer composition comprises a fluorescent agent. Optionally the polymer composition comprises a fluorescent agent between 1-5%. Optionally the polymer composition comprises a fluorescent agent between 1.5-4%. Optionally the polymer composition comprises a fluorescent agent between 2-3%.

Optionally the polymer comprises at least one monomer of the group comprising isobornyl acrylate, urethane acrylate, urethane methacrylate, acrylamide, and N,N-dimethylacrylamide. Optionally the polymer comprises Isobornyl acrylate between 15-70%. Optionally the polymer comprises urethane (meth)acrylate between 15-70%. Optionally the polymer comprises N,N-dimethylacrylamide between 5-50%. Optionally the polymer comprises Isobornyl acrylate between 20-60%. Optionally the polymer comprises urethane (meth)acrylate between 20-60%. Optionally the polymer comprises N,N-dimethylacrylamide between 10-40%. Optionally the polymer comprises Isobornyl acrylate between 25-50%. Optionally the polymer comprises urethane (meth)acrylate between 25-50%. Optionally the polymer comprises N,N-dimethylacrylamide between 15-30%. Optionally the polymer comprises Isobornyl acrylate between 30-45%. Optionally the polymer comprises urethane (meth)acrylate between 30-45%. Optionally the polymer comprises N,N-dimethylacrylamide between 20-25%. Optionally the polymer comprises Isobornyl acrylate between 35-40%. Optionally the polymer comprises urethane (meth)acrylate between 35-40%.

Optionally the polymer composition comprises a photoinitiator. Optionally the polymer composition comprises a photoinitiator between 1-5%. Optionally the polymer composition comprises a photoinitiator between 1.5-4%. Optionally the polymer composition comprises a photoinitiator between 2-3%. It will be appreciated that the photoinitiator may be any known photoinitiator. Selection of the best individual photoinitiator or combination of photoinitiator is dependent on a number of variables including chemistry of the polymer composition, (polyester, epoxy acrylate, urethane acrylate), selection of monomers (monofunctional, multifunctional acrylate monomers), UV lamp type and orientation, cure speed required, coating property requirements, substrate and many others. A skilled person is well able to determine suitable photoinitiators. Optionally the photoinitiator is a UV photoinitiator. Optionally the photoinitiator is visible light photoinitiator. Optionally the photoinitiator is selected from the group consisting of alpha hydroxyketone, bis acyl phosphine oxide, alpha aminoketone, benzoin ether, benzyl ketal, alpha-dialkoxy-aceto-phenone, alpha-hydroxy-alkyl-phenone, alpha-amino-alkyl-phenone, benzo-phenone, benzoamine, thioxanthone, thioamine, and metalloocene.

Optionally the polymer composition is a UV curable resin. Optionally the polymer composition is a polymer or resin selected from the group consisting of Dymax 1161-M, DYMAX 1128 M, DYMAX, 1163, DYMAX 1180-M, DYMAX 1193-M-SV04, Henkel 3211, Henkel 3201, Henke 3311, DYMAX 1403-M, DYMAX 1404-M-UR, DYMAX 1-20793, ThreeBond 2202 C. For the purpose of the invention polymer composition and resin are used interchangeably and mean a composition comprising at least one polymer.

Optionally the polymer composition is substantially free of estrogenic chemicals. Optionally the polymer composition is substantially free of bisphenol-A.

Optionally the polymer composition has a viscosity at 20 rpm of 200 cP-400 cP prior to irradiation. Optionally the polymer composition has a viscosity at 20 rpm of 250 cP-350 cP prior to irradiation. Optionally the polymer composition has a viscosity at 20 rpm of 280 cP-320 cP prior to irradiation. The viscosity is measured at room temperature.

Optionally the first time period is sufficient to cure 1-100% of the polymer in polymer composition. Optionally the first time period is sufficient to cure 10-90% of the polymer in polymer composition. Optionally the first time period is sufficient to cure 20-80% of the polymer in polymer composition Optionally the first time period is sufficient to cure 30-70% of the polymer in polymer composition. Optionally the first time period is sufficient to cure 40-60% of the polymer in polymer composition. Optionally the first time period is sufficient to cure 45-55% of the polymer in polymer composition. Optionally the first time period is 0.1-10 seconds. Optionally the first time period is 0.5-5 seconds. Optionally the first time period is 0.8-3 seconds. Optionally the first time period is 1-2 seconds.

Optionally one of the objects is a plastic needle hub.

Optionally the plastic is a copolyester. Optionally the copolyester is a copolymer of a polyester in combination with diacids monomers and/or diol monomers. Common diacids are Terephthalic acid (TPA) and isophthalic acid (IPA). Common diols are Ethylene Glycol (EG), cyclohexane dimethanol (CHDM), butane diol. Optionally the copolyester is selected from the group consisting of, Polyethylene terephthalate (PET), Polyethylene terephthalate glycol-modified (PETG), Polycyclohexylenedimethylene 1 terephthalate (PCT), Polycyclohexylenedimethylene 1 terephthalate glycol-modified (PCTG), Polycyclohexylenedimethylene 1 terephthalate isophtalic acid modified (PCTA), Polybutylene terephthalate (PBT). Commonly used copolyester include Tritan, Eastar, Provista, Findley, Vylon, Dynapol, Skybon, and Petaflex. Optionally the plastic is permeable for UV and/or .gamma radiation Optionally the plastic is substantially free of bisphenol-A.

Optionally the metal is stainless steel. Optionally one of the objects is plastic and one of the objects is metal. Optionally the plastic object is a hub. Optionally the metal object is a needle or cannula. Optionally the plastic object is a hub and the metal object is a needle or cannula. Optionally the plastic and metal object form a hypodermic needle or cannula.

In another aspect the invention is related to a system comprising a plastic object and a metal object connected by a polymer composition, wherein the plastic object and the metal object are connected according to the method of the first aspect and/or any of the options thereof of the invention.

Optionally the system comprises a needle or cannula wherein the plastic object is a hub and the metal object is needle or cannula. Optionally the system is a hypodermic needle or cannula. Optionally the needle or cannula has a gauge of between 7-34. Optionally the needle or cannula has a gauge of between 9-31. Optionally the needle or cannula has a gauge of between 10-29. Optionally the needle or cannula has a gauge of between 11-27. Optionally the needle or cannula has a gauge of between 13-25. Optionally the needle or cannula has a gauge of between 15-23. Optionally the needle or cannula has a gauge of between 17-21. Optionally the needle or cannula has a gauge of between 18-20.

Optionally in the system one of the objects has a surface to volume ratio of 0.005 $mm^2/mm^3$-40 $mm^2/mm^3$. Optionally in the system one of the objects has a surface to volume ratio of 0.2 $mm^2/mm^3$-27 $mm^2/mm^3$. Optionally in the system one of the objects has a surface to volume ratio of 2.5 $mm^2/mm^3$-13.5 $mm^2/mm^3$.

Optionally in the system the plastic and/or the metal object has a cylindrical shape. Optionally in the system the metal and/or plastic object is open ended.

Optionally in the system the polymer composition has received a gamma-radiation dosage of between 5 and 80 kGy. Optionally in the system the polymer composition has received a gamma-radiation dosage of 25 and 50 kGy. Optionally in the system the gamma-radiation dosage provides a sterility assurance level, of at least 2 log reduction for micro-organisms for the plastic object and the metal object. Optionally in the system the gamma-radiation dosage provides a sterility assurance level, of at least 2-12 log reduction for micro-organisms. Optionally in the system the gamma-radiation dosage provides a sterility assurance level, of at least 3-10 log reduction for micro-organisms. Optionally in the system the gamma-radiation dosage provides a sterility assurance level, of at least 4-9 log reduction for micro-organisms. Optionally in the system the gamma-radiation dosage provides a sterility assurance level, of at least 5-8 log reduction for micro-organisms. Optionally in the system the gamma-radiation dosage provides a sterility assurance level, of at least 6-7 log reduction for micro-organisms.

Optionally in the system the polymer composition is provided substantially free of solvents that are capable of a chemical reaction during UV radiation and/or gamma radiation. Optionally in the system the polymer composition is curable under the influence of visible light or UV light, or both. Optionally in the system the polymer composition is fluorescent. Optionally in the system the polymer composition comprises a fluorescent agent. Optionally the polymer composition comprises a fluorescent agent between 1-5%. Optionally the polymer composition comprises a fluorescent agent between 1.5-4%. Optionally the polymer composition comprises a fluorescent agent between 2-3%.

Optionally in the system the polymer comprises at least one monomer of the group comprising isobornyl acrylate, urethane acrylate, urethane methacrylate, acrylamide, and N,N-dimethylacrylamide. Optionally the polymer comprises at least one monomer of the group comprising isobornyl acrylate, urethane acrylate, urethane methacrylate, acrylamide, and N,N-dimethylacrylamide. Optionally the polymer comprises Isobornyl acrylate between 15-70%. Optionally the polymer comprises urethane (meth)acrylate between 15-70%. Optionally the polymer comprises N,N-dimethylacrylamide between 5-50%. Optionally the polymer comprises Isobornyl acrylate between 20-60%. Optionally the polymer comprises urethane (meth)acrylate between 20-60%. Optionally the polymer comprises N,N-dimethylacrylamide between 10-40%. Optionally the polymer comprises Isobornyl acrylate between 25-50%. Optionally the polymer comprises urethane (meth)acrylate between 25-50%. Optionally the polymer comprises N,N-dimethylacrylamide between 15-30%. Optionally the polymer comprises Isobornyl acrylate between 30-45%. Optionally the polymer comprises urethane (meth)acrylate between 30-45%. Optionally the polymer comprises N,N-dimethylacrylamide between 20-25%. Optionally the polymer comprises Isobornyl acrylate between 35-40%. Optionally the polymer comprises urethane (meth)acrylate between 35-40%.

Optionally in the system the polymer composition comprises a photoinitiator. Optionally the polymer composition comprises a photoinitiator between 1-5%. Optionally the polymer composition comprises a photoinitiator between 1.5-4%. Optionally the polymer composition comprises a photoinitiator between 2-3%. It will be appreciated that the photo initiator may be any known photoinitiator. Selection of the best individual photoinitiator or combination of photoinitiator is dependent on a number of variables including chemistry of the polymer composition, (polyester, epoxy acrylate, urethane acrylate), selection of monomers (monofunctional, multifunctional acrylate monomers), UV lamp type and orientation, cure speed required, coating property requirements, substrate and many others. A skilled person is well able to determine suitable photoinitiators. Optionally the photoinitiator is a UV photoinitiator. Optionally the photoinitiator is visible light photoinitiator. Optionally the photoinitiator is selected from the group consisting of alpha hydroxyketone, bis acyl phosphine oxide, alpha aminoketone, benzoin ether, benzyl ketal, alpha-dialkoxy-aceto-phenone, alpha-hydroxy-alkyl-phenone, alpha-amino-alkyl-phenone, benzo-phenone, benzoamine, thioxanthone, thioamine, and metallocene.

Optionally in the system the polymer composition is a UV curable resin. Optionally the polymer composition is a resin selected from the group consisting of Dymax 1161-M, DYMAX 1128 M, DYMAX, 1163, DYMAX 1180-M, DYMAX 1193-M-SV04, Henkel 3211, Henkel 3201, Henke 3311, DYMAX 1403-M, DYMAX 1404-M-UR, DYMAX 1-20793, ThreeBond 2202 C.

Optionally in the system the polymer composition is substantially free of estrogenic chemicals, preferably substantially free of bisphenol-A.

Optionally in the system the polymer composition has a viscosity at 20 rpm of 200 cP-400 cP prior to irradiation. Optionally the polymer composition has a viscosity at 20 rpm of 250 cP-350 cP prior to irradiation. Optionally the polymer composition has a viscosity at 20 rpm of 280 cP-320 cP prior to irradiation. The viscosity is measured at room temperature.

Optionally in the system the polymer composition the polymer composition is a UV curable resin.

Optionally in the system the plastic is a copolyester. Optionally in the system the plastic is permeable for UV and/or .gamma radiation Optionally the copolyester is a copolymer of diacids monomers and/or diol monomers. Common diacids are Terephthalic acid (TPA) and isophthalic acid (IPA). Common diols are Ethylene Glycol (EG), cyclohexane dimethanol (CHDM), butane diol. Optionally the copolyester is selected from the group consisting of, Polyethylene terephthalate (PET), Polyethylene terephthalate glycol-modified (PETG), Polycyclohexylenedimethylene l terephthalate (PCT), Polycyclohexylenedimethylene l terephthalate glycol-modified (PCTG), Polycyclohexylenedimethylene l terephthalate isophtalic acid modified (PCTA), Polybutylene terephthalate (PBT). Commonly used copolyester include Tritan, Eastar, Provista, Findley, Vylon, Dynapol, Skybon, and Petaflex.

Optionally in the system the plastic is substantially free of bisphenol-A. Optionally in the system the metal is stainless steel.

In a further aspect the invention is directed to a cosmetic method for anti-aging skin treatment wherein the method comprises, subcutaneously administering of an effective amount a of a dermal filler or *Botulinum* toxin to an area of skin, wherein the administering is performed by a syringe and a hypodermic needle or cannula of any aspect and/or option thereof of the invention. Optionally the area of skin is an area of the face and/or neck.

In a further aspect the invention is directed to a use of the system according to any aspect and/or any option thereof wherein the system is a needle or cannula system comprising a plastic hub and a metal needle or cannula in a method comprising an injection step. Optionally the method is medical method. Optionally the method is a method of treatment. Optionally the method is a method of diagnosis. Optionally the method is a method comprising an injection selected from the group comprising subcutaneous injection, intramuscular injection, intradermal injection, depot injection, intravenous injection, intraosseous injection, intraperitoneal injection, intrathecal injection, epidural injection, intracardiac injection, intraarticular injection, intracavernous injection, intrvitreal injection, intracocular injection, intracerebral injection, intracerebroventricular injection. Optionally the method is a non-medical use. Optionally the method is a diagnostic method. Optionally the method is a method that does not involve injection of a human. Optionally the method is a method for treatment of a non-human animal. Optionally the method comprises injection of a non-human animal.

In another aspect the invention relates to a hypodermic needle or cannula comprising a needle at least substantially of metal and a hub at least substantially of plastic, the needle and hub coupled to each other by means of a cured polymer composition that is substantially free of bisphenol aceton (BPA), and provides a coupling strength between the needle and hub that withstands a pulling of the needle out of the hub at a push or pulling power on the needle of at least 22N.

In another aspect the invention relates to a hypodermic needle or cannula comprising a needle at least substantially of metal and a hub at least substantially of plastic, the needle and hub coupled to each other by means of a cured polymer composition that is substantially free of bisphenol aceton (BPA) and that provides a bonding strength between the needle and hub which passes a pull out test according to ISO 7864 1993 with a force of at least 22N applied as push or pull in the direction of the needle axis.

Preferably the hypodermic needle or cannula according to the invention has a size of between 21 G-32 G, preferably 21 G, 27 G, 30 G or 32 G.

Optionally the polymer composition in the hypodermic needle or cannula according to the invention is provided substantially free of solvents that are capable of a chemical reaction during UV radiation and/or gamma radiation.

Optionally the polymer composition in the hypodermic needle or cannula according to the invention is curable under the influence of visible light or UV light, or both. Optionally the polymer composition in the hypodermic needle or cannula according to the invention is fluorescent. Optionally the polymer composition in the hypodermic needle or cannula according to the invention comprises a fluorescent agent. Optionally the polymer composition in the hypodermic needle or cannula according to the invention comprises a fluorescent agent between 1-5%. Optionally the polymer composition in the hypodermic needle or cannula according to the invention comprises a fluorescent agent between 1.5-4%. Optionally the polymer composition in the hypodermic needle or cannula according to the invention comprises a fluorescent agent between 2-3%.

Optionally the polymer in the hypodermic needle or cannula according to the invention comprises at least one monomer of the group comprising isobornyl acrylate, urethane acrylate, urethane methacrylate, acrylamide, and N,N-dimethylacrylamide. Optionally the polymer in the hypodermic needle or cannula according to the invention comprises Isobornyl acrylate between 15-70%. Optionally the polymer in the hypodermic needle or cannula according to the invention comprises urethane (meth)acrylate between 15-70%. Optionally the polymer in the hypodermic needle or cannula according to the invention comprises N,N-dimethylacrylamide between 5-50%. Optionally the polymer in the hypodermic needle or cannula according to the invention comprises Isobornyl acrylate between 20-60%. Optionally the polymer in the hypodermic needle or cannula according to the invention comprises urethane (meth)acrylate between 20-60%. Optionally the polymer in the hypodermic needle or cannula according to the invention comprises N,N-dimethylacrylamide between 10-40%. Optionally the polymer comprises Isobornyl acrylate between 25-50%. Optionally the polymer comprises urethane (meth)acrylate between 25-50%. Optionally the polymer comprises N,N-dimethylacrylamide between 15-30%. Optionally the polymer comprises Isobornyl acrylate between 30-45%. Optionally the polymer comprises urethane (meth)acrylate between 30-45%. Optionally the polymer comprises N,N-dimethylacrylamide between 20-25%. Optionally the polymer comprises Isobornyl acrylate between 35-40%. Optionally the polymer in the hypodermic needle or cannula according to the invention comprises urethane (meth)acrylate between 35-40%.

Optionally the polymer composition in the hypodermic needle or cannula according to the invention comprises a photoinitiator. Optionally the polymer composition in the hypodermic needle or cannula according to the invention comprises a photoinitiator between 1-5%. Optionally the polymer composition in the hypodermic needle or cannula according to the invention comprises a photoinitiator between 1.5-4%. Optionally the polymer composition in the hypodermic needle or cannula according to the invention comprises a photoinitiator between 2-3%. It will be appreciated that the photoinitiator may be any known photoinitiator. Selection of the best individual photoinitiator or combination of photoinitiator is dependent on a number of variables including chemistry of the polymer composition, (polyester, epoxy acrylate, urethane acrylate), selection of monomers (monofunctional, multifunctional acrylate monomers), UV lamp type and orientation, cure speed required, coating property requirements, substrate and many others. A skilled person is well able to determine suitable photoinitiators. Optionally the photoinitiator is a UV photoinitiator. Optionally the photoinitiator is visible light photoinitiator. Optionally the photoinitiator is selected from the group consisting of alpha hydroxyketone, bis acyl phosphine oxide, alpha aminoketone, benzoin ether, benzyl ketal, alpha-dialkoxy-aceto-phenone, alpha-hydroxy-alkyl-phenone, alpha-amino-alkyl-phenone, benzo-phenone, benzoamine, thioxanthone, thioamine, and metalloocene.

Optionally the polymer composition in the hypodermic needle or cannula according to the invention is a UV curable resin. Optionally the polymer composition in the hypodermic needle or cannula according to the invention is a polymer or resin selected from the group consisting of Dymax 1161-M, DYMAX 1128 M, DYMAX, 1163, DYMAX 1193-M-SV04, DYMAX 1180-M, Henkel 3211, Henkel 3201, Henke 3311, DYMAX 1403-M, DYMAX 1404-M-UR, DYMAX 1-20793, ThreeBond 2202 C. For the purpose of the invention polymer composition and resin are used interchangeably and mean a composition comprising at least one polymer.

DETAILED DESCRIPTION

According to a first aspect the invention is directed to a method for connecting a first object and a second object by using a polymer composition.

Optionally, the polymer composition is provided as curable under the influence of visible light or UV light or by UV and visible light. Polymer compositions that are curable under UV light and/or visible light are well known. Curing under visible light enables the polymer composition to use photonic energy that is emitted alongside the UV-radiation in the visible light spectrum. Optionally polymer composition is fluorescent, optionally under any UV-radiation Optionally the polymer composition is fluorescent between a wavelength of 320 nm-395 nm. Optionally polymer composition is fluorescent at low intensity UV-radiation such as between 365 nm and the visible spectrum. Optionally polymer composition is fluorescent such that visible light is re-emitted. Optionally the re-emitted visible light is blue light. In this way visible light is disseminated to UV-radiation shielded regions in the polymer composition and regions otherwise blocked from direct irradiation. This has the advantage that it reduces the occurrence of insufficient curing in UV-radiation shielded regions and prevents weak spots. The dissemination of visible light occurs through the absorption and re-emission of high energy photons such as UV-radiation. Other high energy photons such as X-rays or gamma-radiation may through absorption and re-emission as lower energy photons also provide dissemination of photons capable of driving the curing of the UV-cured polymer composition into the final polymer. Optionally the UV radiation is provided by a UV lamp. Suitably UV lamps include fluorescent lamps, mercury vapor lamps with or without additives such as iron or gallium. Fluorescence lamps have the advantage that they do not produce as much heat as a mercury lamp. Optionally the UV radiation is provided by a LED UV lamp. UV LED devices are capable of emitting a narrow spectrum of radiation (+/−10 nm), while mercury lamps have a broader spectral distribution. Further advantages of UV LED include lasting for over 20,000 hours, no downtime to change lamps, instant on/of, containing no mercury. In addition, LED produces no ozone gas and thus obviates ventilation.

The method further includes applying the polymer composition to at least part of the surface of at least one of the first object or second object. Depending on the object substantially the whole or only a part of the surface is covered with polymer composition. Optionally 0.1-100% of the surface is coated with polymer composition. Optionally 1-90% of the surface is coated with polymer composition. Optionally 2-80% of the surface is coated with polymer composition. Optionally 3-70% of the surface is coated with polymer composition. Optionally 4-60% of the surface is coated with polymer composition. Optionally 5-50% of the surface is coated with polymer composition. Optionally 6-45% of the surface is coated with polymer composition. Optionally 7-40% of the surface is coated with polymer composition. Optionally 8-35% of the surface is coated with polymer composition. Optionally 9-30% of the surface is coated with polymer composition. Optionally 10-25% of the surface is coated with polymer composition. Optionally 12-20% of the surface is coated with polymer composition.

Optionally at least part of the surface of the first object is coated with polymer composition. Optionally at least part of the surface of the second object is coated with polymer composition. Optionally at least part of the surface of the first object and at least part of the surface of the second object is coated with polymer composition.

The method further includes connecting the first object and the second object at the surface where the polymer composition is applied. Optionally the first and second object are close to each other and the polymer composition is applied in the space between the first and second object.

The method further includes irradiating the polymer composition using UV-radiation over a first time period. Optionally the first time period is sufficient to cure 1-100% of the polymer in polymer composition. Optionally the first time period is sufficient to cure 10-90% of the polymer in polymer composition. Optionally the first time period is sufficient to cure 20-80% of the polymer in polymer composition Optionally the first time period is sufficient to cure 30-70% of the polymer in polymer composition. Optionally the first time period is sufficient to cure 40-60% of the polymer in polymer composition. Optionally the first time period is sufficient to cure 45-55% of the polymer in polymer composition. Optionally the first time period is between 1 ms and 100 s. Optionally the first time period is between 100 ms and 10 s. Optionally the first time period is between 0.5 s and 2.5 s. Optionally the first time period is between 1 s and 2 s. Irradiating the polymer composition with UV-radiation allows for at least the partial curing or hardening of the resin or polymer composition. It will be appreciated that the first time period is chosen such that the first object and the second object are connected such that the polymer composition and the interfaces of the first and second object that are connected to each other via the polymer composition are able to withstand at least gravitational forces which are exerted on the first and second object. Optionally the connection obtained by the UV irradiation of the polymer composition is sufficient to withstand between 5-70 N/m of pulling force. Optionally the connection obtained by the UV irradiation of the polymer composition is sufficient to withstand between 30-60 N/m. It will be appreciated that the pulling force is exerted along the bonding surfaces of the first and second object such that a sheer stress is exerted on the connection created by the irradiation of the polymer composition.

The method further comprises irradiating UV radiated polymer composition with gamma-radiation over a second time period. Gamma radiation, also known as gamma rays, refers to electromagnetic radiation of an extremely high frequency and therefore consists of high-energy photons. Gamma rays are ionizing radiation. Gamma rays typically have frequencies above 10 exahertz (or $>10^{19}$ Hz), and therefore have energies above 100 keV and wavelengths less than 10 picometers ($10^{-12}$ meter), For the purpose of the present invention, gamma radiation includes X-rays. Gamma-radiation is beneficially absorbed and re-emitted as X-rays. Irradiation with high-energy photons is thereby intensified at and near the object-polymer interface. Surprisingly irradiation of the polymer by gamma-radiation provided a stronger connection of the objects by the polymer composition. Without wishing to be bound to theory, in the case of UV-radiation the local UV-intensity in the polymer decreases with increasing depth of the polymer layer. In some cases this may result in the non-homogeneous curing of the polymer. The polymer near the object interface in particular may be poorly reached by UV-radiation at increased polymer layer thickness. Irradiation with gamma rays may reduce the prevalence of uncured regions in the gamma irradiated polymer compared to the UV irradiated polymer Suitably gamma irradiation uses Cobalt 60 or cesium-137 radiation. Optionally the gamma radiation has an energy of 1 keV to about 30 MeV. Optionally the gamma radiation has an energy of 0.2 MeV to about 10 MeV.

The advantage of the method of the invention is that independent of the size of the objects, a uniform time may be used for the UV irradiation and the gamma irradiation. Especially for milliscopic objects, such as a needle hub, and a needle, the time of UV radiation is independent of the gauge. It will be appreciated that time uniform means that the first time period and second time period may remain substantially the same invariable even when the confronting surfaces of the objects varies. For example in the case of a needle and a needle hub, the first time period and second time period is independent of the needle gauge. The first time period and second time period may be constant independent whether the outer diameter of the needle is between 0.2 mm and 1.5 mm or optionally between 0.41-1.25 mm or optionally between 0.41-0.81 mm. This enables a variety of needles to be joined using the same process simultaneously or without changes the process parameters. It will further be appreciated that this also applies to other objects.

Optionally, the irradiation with gamma-radiation is sufficient for the sterilization of the objects. This has the benefit of allowing a sterilization to be accomplished simultaneously with the final curing and hardening of the polymer composition. It will be appreciated that sterilization here is gamma-sterilization. Optionally, gamma sterilization is performed using Cobalt-60 or cesium-137 as radioisotope. It will be appreciated that the gamma-sterilization is sufficient to ensure the total elimination of microorganisms, optionally all. Optionally the polymer composition has received a gamma-radiation dosage of between 5 and 80 kGy. Optionally the polymer composition has received a gamma-radiation dosage of 25 and 50 kGy. A skilled person is well able to determine the radiation dosage depending on the energy of the gamma radiation and the time of the radiation. Optionally the gamma-radiation dosage provides a sterility assurance level, of at least 2 log reduction for microorganisms for the plastic object and the metal object. Optionally the gamma-radiation dosage provides a sterility assurance level, of at least 2-12 log reduction for microorganisms. Optionally the gamma-radiation dosage provides a sterility assurance level, of at least 3-10 log reduction for micro-organisms. Optionally the gamma-radiation dosage provides a sterility assurance level, of at least 4-9 log reduction for micro-organisms. Optionally the gamma-radiation dosage provides a sterility assurance level, of at least 5-8 log reduction for micro-organisms. Optionally the gamma-radiation dosage provides a sterility assurance level, of at least 6-7 log reduction for micro-organisms. Combining sterilization and curing is time saving in a production process. It will be appreciated that instead of gamma-irradiation both partial and total sterilization can alternatively be accomplished using dry heating, (pressured) vapour, ethylene oxide, ozone, formaldehyde, gas plasma, peracetic acid, and e-beam. Optionally, the radiation dosage is chosen such that objects and final polymer comply with healthcare standards for hypodermic use after the second time period. Optionally, the gamma-radiation dosage is chosen such that that the polymer and objects retain their thermal-oxidative stability during gamma-irradiation. It will be appreciated that the gamma-radiation dosage is limited such that the physical integrity of the polymer, objects such as plastic part or metal part is prevented from being compromised by intense gamma-irradiation. At least such that the connection between objects such as the metal and plastic (the metal-polymer and plastic-polymer interfaces and the polymer itself) is prevented from decreasing below 50 N/m outer diameter of a cylindrical object or equivalent thereof for non-cylindrical shapes.

Optionally, gamma-radiation may be applied such that non-biocompatible reactants are eliminated from the UV-radiated polymer which would otherwise remain at the end of UV-irradiation, such that the UV-radiated polymer is made substantially free of non-biocompatible reactants. This has the benefit of allowing medical usage of the final polymer, such as in dental implants and-or hypodermic needles or cannulas.

The method of the invention allows objects, such as plastic parts of different sizes, and metal parts of different sizes to be connected or joined using substantially the same UV-irradiation time. It will be appreciated that this applies especially to milliscopic objects, such as plastic hubs and metal needles. The method of the invention is especially suitable for object having a surface to volume ratio of 0.2 $mm^2/mm^3$-27 $mm^2/mm^3$, optionally a surface to volume ratio of 2.5 $mm^2/mm^3$-13.5 $mm^2/mm^3$. It is to be understood that for cylindrical objects such as needles and needle hubs, the volume is taken to mean the volume enclosed by the outer surface of the cylinder. In the case of an open ended cylindrical volume, the volume of the cylinder is taken as if it were not open ended. Optionally, the one of the objects has a cylindrical shape. Optionally the second object encloses at least a part of the outer surface of the first object. Optionally the first object and the second object are concentrically connected or joined. Optionally, the one of the objects is open ended at two opposite ends.

Optionally the objects, such as the plastic, for example a needle hub, and the metal part, such as a needle, are substantially free of bisphenol-A. Bisphenol-A or BPA is generally prevalent in epoxy resins and plastics. However, due to the hormone-like qualities of BPA the use thereof has been heavily legislated. Medical systems and devices, in particular medical equipment which are used invasively to the human body, such as hypodermic needles, are require to be substantially free of BPA. Also in non-medically related products, such as child care products the use of BPA is heavily restricted. In this manner, the polymer complies with medical standards for use in medical tools. Optionally for medical uses, the objects to be connected are moisture resistant.

Optionally, the plastic part is substantially free of bisphenol-A. Optionally, the plastic part is provided as a needle hub. In order for a needle to be used on a syringe the needle or cannula must be secured in a needle hub. The needle hub forms a stable base with which the needle can be connected to a mouthpiece of a syringe. For the purpose of the present invention whenever needle is used in the application, a cannula is meant to be included. A needle hub can for example be provided as a stylet hub in a catheter where the stylet hub can be joined to a metal stylet. It will be appreciated that the stylet is a type of needle. The needle hub is preferably a polypropylene (PP)-polymer or a copolyester such as Triton MX711. Optionally, the PP-polymer is provided as gamma-stabilized PP. Optionally the copolyester is a copolymer of a polyester in combination with diacids monomers and/or diol monomers. Common diacids are Terephthalic acid (TPA) and isophthalic acid (IPA). Common diols are Ethylene Glycol (EG), cyclohexane dimethanol (CHDM), butane diol. Optionally the copolyester is selected from the group consisting of, Polyethylene terephthalate (PET), Polyethylene terephthalate glycol-modified (PETG), Polycyclohexylenedimethylene 1 terephthalate (PCT), Polycyclohexylenedimethylene 1 terephthalate glycol-modified (PCTG), Polycyclohexylenedimethylene 1 terephthalate isophtalic acid modified (PCTA), Polybutylene terephthalate (PBT). Commonly used copolyester include Tritan, Eastar, Provista, Findley, Vylon, Dynapol, Skybon, and Petaflex. Optionally the plastic is permeable for UV and/or .gamma radiation. Suitable plastics are TRITAN MX711, TOPAS 6013S-04 or ZEONEX 690R.

Both Triton MX711 and PP-resin have the benefit of being a low price durable plastic enhancing the longevity of the plastic part. Triton MX711 is beneficially physically stable during gamma-irradiation up to sterilization dosages and is further transparent to UV-radiation such that UV-absorption is prevented in the plastic part or needle hub.

Optionally, one of the objects is a e metal part. Optionally one of the objects is a needle. Optionally the needle is a stainless steel. Optionally the needle or cannula has a diameter of between 0.1 mm-2 mm. Optionally the needle or cannula has a gauge of between 7-34. Optionally the needle or cannula has a gauge of between 9-31. Optionally the needle or cannula has a gauge of between 10-29. Optionally the needle or cannula has a gauge of between 11-27. Optionally the needle or cannula has a gauge of between 13-25. Optionally the needle or cannula has a gauge of between 15-23. Optionally the needle or cannula has a gauge of between 17-21. Optionally the needle or cannula has a gauge of between 18-20.

Optionally, the polymer, is substantially free of solvents that may react during any of the irradiation. Optionally any solvents in the polymer composition are decomposed by the UV radiation or gamma radiation or by both. This has the benefit of preventing or at least reducing the presence of solvents or chemicals which remain in the final cured polymer as a residual after the gamma irradiation. This has advantages with respect to biocompatibility. A further benefit is that after gamma radiation no solvents remain, further drying steps, aimed at expelling the remaining solvent, are therefor no longer required.

Optionally the polymer composition is substantially free of any estrogenic chemicals, such as, but not limited to, bisphenol-A (BPA). This has the benefit of avoiding health risks attached to exposure to estrogenic chemicals. Optionally the polymer composition is in particular substantially free of bisphenol-A.

Optionally, the polymer comprises acrylated urethane or methacrylated urethane. This has the benefit that the polymer is susceptible to UV-irradiation. Urethane (meth)acrylate oligomer further has a glass transition temperature of approximately 180-195° C. UV-cured Urethane (meth)acrylate oligomer is thermally stable below these temperatures. This bestows the benefit of allowing the polymer to remain thermally stable during both UV and gamma-irradiation.

Optionally, the polymer has a viscosity at 20 rpm of 200 cP-400 cP prior to any curing or irradiation. In this way any unwanted spread beyond a desired bonding surface is prevented such that clogging, contamination or effecting a functional property is prevented. A viscosity of 200-400 cP further provides an increased resistance to creep as a result of gravitational forces, with respect to polymers of lower viscosity. This allows for connecting object where the surface of the objects where the polymer is applied, such as a plastic object or a metal object, are substantially parallel to the direction of gravitational forces.

Optionally the polymer composition is curable under the influence of visible light or UV light, or both. Optionally the polymer composition is fluorescent. Optionally the polymer composition comprises a fluorescent agent. Optionally the polymer composition comprises a fluorescent agent between 1-5%. Optionally the polymer composition comprises a fluorescent agent between 1.5-4%. Optionally the polymer composition comprises a fluorescent agent between 2-3%.

Optionally the polymer comprises at least one monomer of the group comprising isobornyl acrylate, urethane acrylate, urethane methacrylate, acrylamide, and N,N-dimethylacrylamide. Optionally the polymer comprises at least one monomer of the group comprising isobornyl acrylate, urethane acrylate, urethane methacrylate, acrylamide, and N,N-dimethylacrylamide. Optionally the polymer comprises Isobornyl acrylate between 15-70%. Optionally the polymer comprises urethane (meth)acrylate between 15-70%. Optionally the polymer comprises N,N-dimethylacrylamide between 5-50%. Optionally the polymer comprises Isobornyl acrylate between 20-60%. Optionally the polymer comprises urethane (meth)acrylate between 20-60%. Optionally the polymer comprises N,N-dimethylacrylamide between 10-40%. Optionally the polymer comprises Isobornyl acrylate between 25-50%. Optionally the polymer comprises urethane (meth)acrylate between 25-50%. Optionally the polymer comprises N,N-dimethylacrylamide between 15-30%. Optionally the polymer comprises Isobornyl acrylate between 30-45%. Optionally the polymer comprises urethane (meth)acrylate between 30-45%. Optionally the polymer comprises N,N-dimethylacrylamide between 20-25%. Optionally the polymer comprises Isobornyl acrylate between 35-40%. Optionally the polymer comprises urethane (meth)acrylate between 35-40%.

Optionally the polymer composition comprises a photoinitiator. Optionally the polymer composition comprises a photoinitiator between 1-5%. Optionally the polymer composition comprises a photoinitiator between 1.5-4%. Optionally the polymer composition comprises a photoinitiator between 2-3%. It will be appreciated that the photo initiator may be any known photoinitiator. Selection of the best individual photoinitiator or combination of photoinitiator is dependent on a number of variables including chemistry of the polymer composition, (polyester, epoxy acrylate, urethane acrylate), selection of monomers (monofunctional, multifunctional acrylate monomers), UV lamp type and orientation, cure speed required, coating property requirements, substrate and many others. A skilled person is well able to determine suitable photoinitiators. Optionally the photoinitiator is a UV photoinitiator. Optionally the photoinitiator is visible light photoinitiator. Optionally the photoinitiator is selected from the group consisting of alpha hydroxyketone, bis acyl phosphine oxide, alpha aminoketone, benzoin ether, benzyl ketal, alpha-dialkoxy-aceto-phenone, alpha-hydroxy-alkyl-phenone, alpha-amino-alkyl-phenone, benzo-phenone, benzoamine, thioxanthone, thioamine, and metalloocene.

Optionally the polymer composition is a polymer selected from the group consisting of Dymax 1161-M, DYMAX 1128 M, DYMAX, 1163, DYMAX 1180-M, DYMAX 1193-M-SV04, Henkel 3211, Henkel 3201, Henke 3311, DYMAX 1403-M, DYMAX 1404-M-UR, DYMAX 1-20793, ThreeBond 2202C.

TABLE 1

| Commonly used Photoinitiator | |
|---|---|
| Acetophenone, 99% | Anisoin, 95% |
| Anthraquinone, 97% | Anthraquinone-2-sulfonic acid, sodium salt monohydrate, 97% |
| (Benzene) tricarbonylchromium, 98% | Benzil, 98% |
| Benzoin, sublimed, 99.5+% | Benzoin ethyl ether, 99% |
| Benzoin isobutyl ether, tech., 90% | Benzoin methyl ether, 96% |
| Benzophenone, 99% | Benzophenone/1-Hydroxycyclohexyl phenyl ketone, 50/50 blend |
| 3 3,3',4,4'-Benzophenonetetracarboxylic dianhydride, sublimed, 98% | 4-Benzoylbiphenyl, 99% |
| 2-Benzyl-2-(dimethylamino)-4'-morpholinobutyrophenone, 97% | 4,4'-Bis(diethylamino)benzophenone, 99+% |
| 4,4'-Bis(dimethylamino)benzophenone, 98% | Camphorquinone, 98% |
| Chlorothioxanthen-9-one, 98% | (Cumene)cyclopentadienyliron(II) hexafluorophosphate, 98% |
| Dibenzosuberenone, 97% | 2,2-Diethoxyacetophenone, 95% |
| 4,4'-Dihydroxybenzophenone, 99% | 2,2-Dimethoxy-2-phenylacetophenone, 99% |
| 4-(Dimethylamino)benzophenone, 98% | 4,4'-Dimethylbenzil, 97% |
| 2,5-Dimethylbenzophenone, tech., 95% | 3,4-Dimethylbenzophenone, 99% |
| Diphenyl(2,4,6-trimethylbenzoyl)phosphine oxide/2-Hydroxy-2-methyl-propiophenone, 50/50 blend | 4'-Ethoxyacetophenone, 98% |
| 2-Ethylanthraquinone, 97+% | Ferrocene, 98% |
| 3'-Hydroxyacetophenone, 99+% | 4'-Hydroxyacetophenone, 99% |
| 3-Hydroxybenzophenone, 99% | 4-Hydroxybenzophenone, 98% |
| 1-Hydroxycyclohexyl phenyl ketone, 99% | 2-Hydroxy-2-methylpropiophenone, 97% |
| 2-Methylbenzophenone, 98% | 3-Methylbenzophenone, 99% |
| Methybenzoylformate, 98% | 2-Methyl-4'-(methylthio)-2-morpholinopropiophenone, 98% |
| Phenanthrenequinone, 99+% | 4'-Phenoxyacetophenone, 98% |
| Thioxanthen-9-one, 98% | Triarylsulfonium hexafluoroantimonate salts, mixed, 50% in propylene carbonate |
| Triarylsulfonium hexafluorophosphate salts, mixed, 50% in propylene carbonate | |

Optionally the polymer complies with the RoHS Directives 2002/95/EC and 203/11EC, enabling the use of this polymer in medical products such as hypodermic needles. Optionally the polymer composition has a high biocompatibility. Optionally, the fully cured polymer is biocompatibility and tested in accordance with ISO 10993 and USP Class VI.

It will be appreciated that other medical objects and non-medical objects which require connecting a plastic object and a metal object are hereby included. The method of the invention has the benefit of allowing production steps such as the connecting the objects, such as the needle to the needle-hub and preparation for use, such as sterilization, to occur simultaneously.

In another aspect the invention is directed to a system comprising a plastic object and a metal object which are connected by a polymer composition, according to any of the first aspect of the invention and/or options thereof. Optionally the system is a needle or cannula system wherein the plastic object is a hub and the metal object is needle or cannula. Optionally the system is a hypodermic needle or cannula. Optionally the needle or cannula has a gauge of between 7-34. Optionally in the system the metal object has a surface to volume ratio of between 0.005 $mm^2/mm^3$-40 $mm^2/mm^3$. Optionally in the system the metal object has a surface to volume ratio of between 0.2 $mm^2/mm^3$-27 $mm^2/mm^3$. Optionally in the system the metal object has a surface to volume ratio of between 2.5 $mm^2/mm^3$-13.5 $mm^2/mm^3$. Optionally in the system the plastic and-or the metal object has a cylindrical shape. Optionally in the system the metal object is open ended.

Optionally in the system the polymer comprises at least one monomer of the group comprising isobornyl acrylate, urethane acrylate, urethane methacrylate, acrylamide, and N,N-dimethylacrylamide. Optionally in the system the polymer composition is substantially free of estrogenic chemicals. Optionally in the system the polymer composition is substantially free of bisphenol-A. Optionally the polymer composition is a polymer selected from the group consisting of Dymax 1161-M, DYMAX 1128 M, DYMAX, 1163, DYMAX 1180-M, DYMAX 1193-M-SV04, Henkel 3211, Henkel 3201, Henke 3311, DYMAX 1403-M, DYMAX 1404-M-UR, DYMAX 1-20793, ThreeBond 2202C.

Optionally in the system the plastic is a copolyester. Optionally in the system the plastic is a permeable for UV and/or .gamma radiation. Optionally in the system the plastic is substantially free of bisphenol-A.

Optionally in the system the metal is stainless steel.

It is to be understood that any option for the method as indicated above may mutatis muntandis be applied to the system of the invention.

In a further aspect the invention is directed to a cosmetic method for anti-aging skin treatment wherein the method comprises, subcutaneously administering of an effective amount a of a dermal filler or *Botulinum* toxin to an area of skin, wherein the administering is performed by a hypodermic needle or cannula of aspects and/or options of the present invention.

Optionally the area of skin is an are of the face and/or neck. Suitable dermal fillers are soft tissue fillers, which include fat, collagen and hyaluronic acid (Restylane®, Juvederm®), and may be injected into deeper wrinkles on the face. They plump and smooth out wrinkles and furrows and give the skin more volume. Suitable fillers are described in WO2012052562 A1, US20130196944 A1, WO2013028904 A2. Method for antiaging are described in WO02015011204 A1, WO2008072229 A2, US20070079838 A1.

In a further aspect the invention is directed to a use of the system according to any aspect and/or any option thereof wherein the system is a needle or cannula system comprising a plastic hub and a metal needle or cannula in a method comprising an injection step. Optionally the method is medical method. Optionally the method is a method of treatment. Optionally the method is a method of diagnosis. Optionally the method is a method comprising an injection selected from the group comprising subcutaneous injection, intramuscular injection, intradermal injection, depot injection, intravenous injection, intraosseous injection, intraperitoneal injection, intrathecal injection, epidural injection, intracardiac injection, intraarticular injection, intracavernous injection, intrvitreal injection, intracocular injection, intracerebral injection, intracerebroventricular injection. Optionally the method is a non-medical use. Needles may be used in a laboratory setting for applying samples onto a column, gel, filter, measuring device. Needles may also be used to administer compounds to a compositions such as media, solutions, gels. Optionally the method is a diagnostic method. Optionally the method is a method that does not involve injection of a human. Optionally the method is a method for treatment of a non-human animal. Optionally the method comprises injection of a non-human animal.

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention.

For the purpose of clarity and a concise description features are described herein as part of the same or separate embodiments, however, it will be appreciated that the scope of the invention may include embodiments having combinations of all or some of the features and options as described herein.

Figure 1:
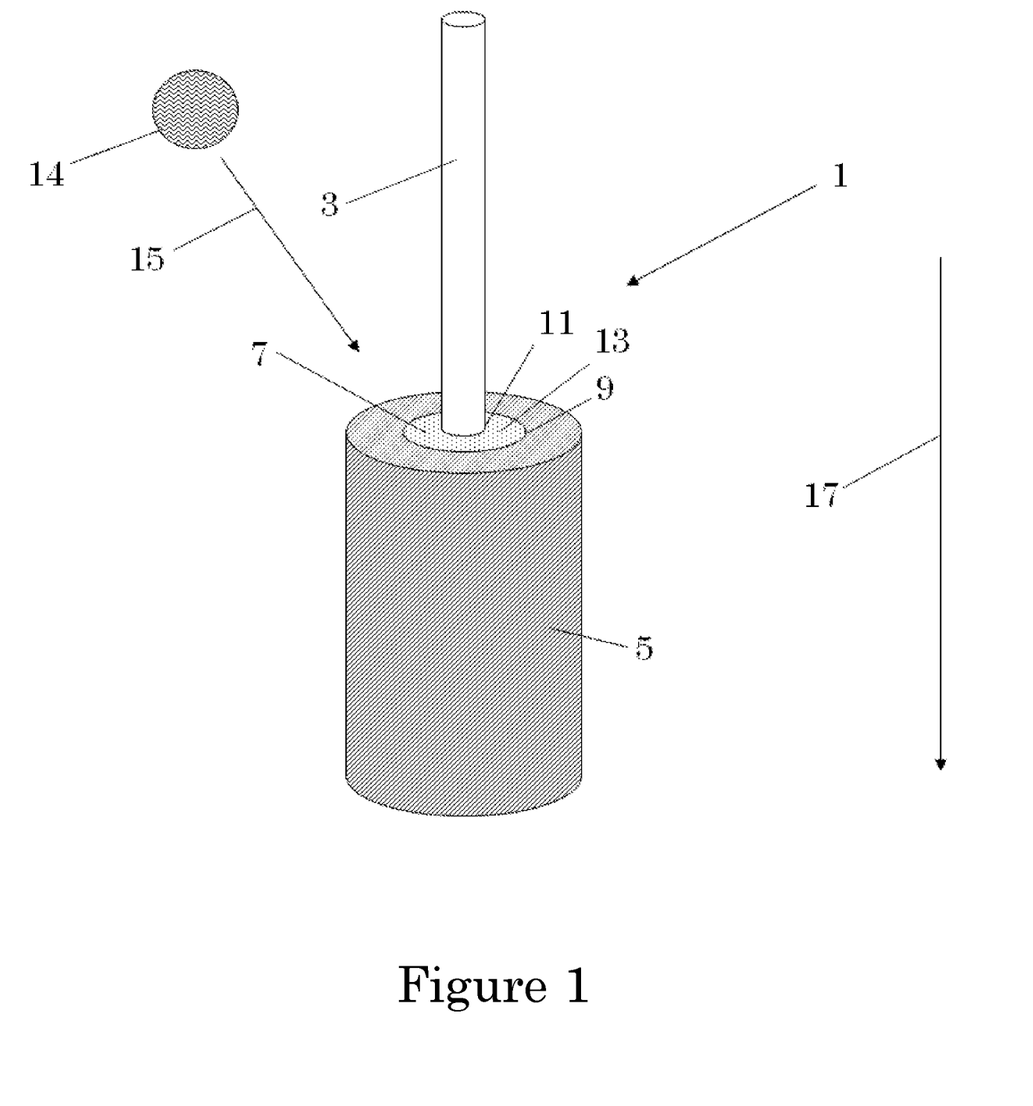
FIG. 1 schematically shows a needle system during UV-irradiation.

In FIG. 1 a hypodermic needle 1 can be seen containing a needle 3, a needle-hub 5 joined by a UV-curable resin 7. The needle 3 is made out of stainless steel. The needle-hub 5 is made out of copolyester Tritan MX711. The resin 7 is DYMAX 1161-M as produced by DYMAX Europe GmbH, Frankfurt am main, Germany. This figure captures a moment during the UV-irradiation step 19 of the hypodermic needle 1. Here the hypodermic needle 1 is placed in an upright position with respect to the direction of gravity 17. As a result the interfaces 9, 11 of the resin with the hub 5 and needle 3 respectively are parallel to the direction of gravity 17. Prior to UV-irradiation the resin 7 was applied to area 13, where the resin 7 was able to spread in the direction of gravity along the outer surface of the needle 3 and along the inner surface of the hub. This extended the interfaces 9, 11 along the direction of spread. UV-irradiation occurs using a UV-source 14 overhead. The hypodermic needle 1 is thereby irradiated from a certain UV-irradiation direction 15.

Figure 2:
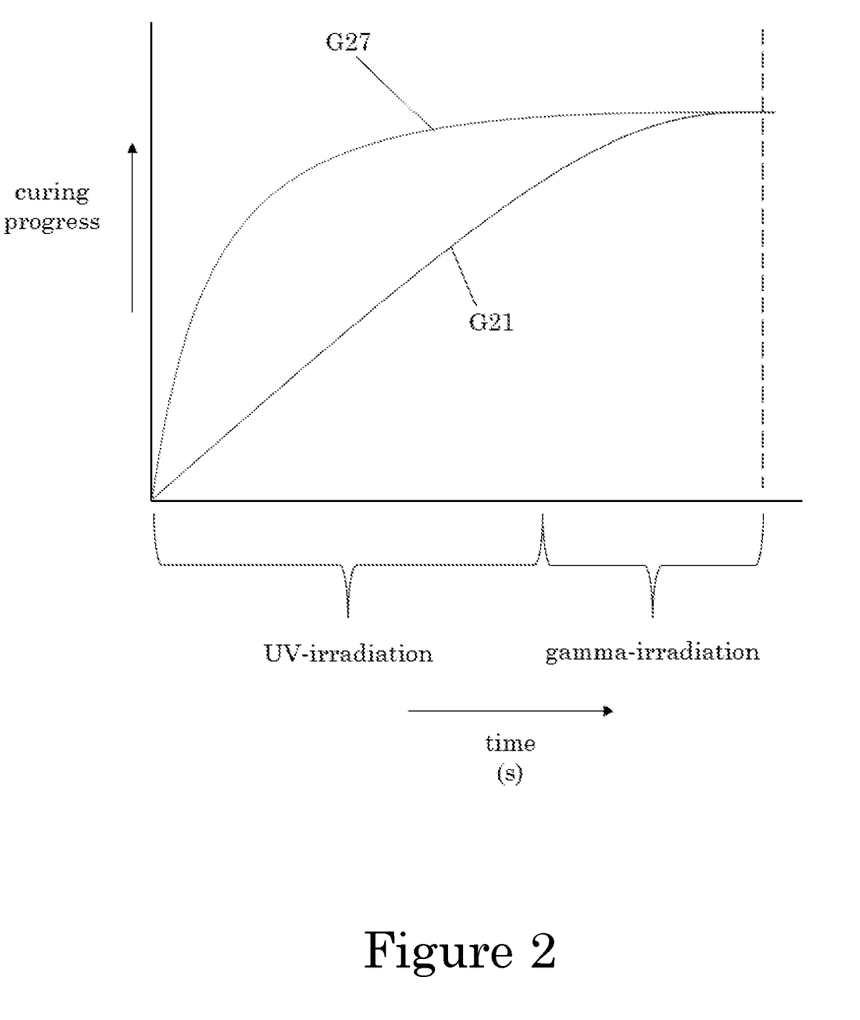
FIG. 2 schematically shows the curing progress over time for needle systems G21 and G27.

In FIG. 2 the curing progress of two hypodermic needles is given, one of a G21 and another of a G27 hypodermic needle. The diameter of the G27 type hypodermic needle is smaller than the diameter of the G21 type hypodermic needle. The curing progress is expressed as a percentage of pulling force which any of the needles G21 and G27 can resist at any of the respective is able to resist at a given moment in time. It can be seen from FIG. 2 that needles of a diameter differing to another can be fully cured simultaneously in the same process.

It is thus believed that the operation and construction of the present invention will be apparent from the foregoing description and drawings appended thereto. For the purpose of clarity and a concise description features are described herein as part of the same or separate embodiments, however, it will be appreciated that the scope of the invention may include embodiments having combinations of all or some of the features described. It will be clear to the skilled person that the invention is not limited to any embodiment herein described and that modifications are possible which may be considered within the scope of the appended claims. Also kinematic inversions are considered inherently disclosed and can be within the scope of the invention. In the claims, any reference signs shall not be construed as limiting the claim. The terms 'comprising' and 'including' when used in this description or the appended claims should not be construed in an exclusive or exhaustive sense but rather in an inclusive sense. Thus expression as 'including' or 'comprising' as used herein does not exclude the presence of other elements, additional structure or additional acts or steps in addition to those listed. Furthermore, the words 'a' and 'an' shall not be construed as limited to 'only one', but instead are used to mean 'at least one', and do not exclude a plurality. Features that are not specifically or explicitly described or claimed may additionally be included in the structure of the invention without departing from its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. To the extend that structure, material, or acts are considered to be essential they are inexpressively indicated as such. Additions, deletions, and modifications within the purview of the skilled person may generally be made without departing from the scope of the invention, as determined by the claims.

EXAMPLES

A pull out test is performed to compare bonding strength of polymer for metal needle and plastic hub.

Glue is DYMAX 1161-M;

UV irradiator: Blue wave LED Prime UVA spot-Curing system and φ3 liquid light guide, 4 branched (2 out of 4 were used) 1.5 m. UV curing time is 2 seconds or as indicated, from both sides at an angle of 45° at 2 mm distance.

Needle size is as indicated.

Hubs used: A8 hub Tritan resin MX711 and Hypodermic Hub from polypropylene resin (PP).

Pull out test is performed after UV curing and with and without additional radiation with gamma radiation (25-50 kGy).

The pull out test measures the force (N) needed to pull out the needle from the hub. The force is applied as push or pull in the direction of the needle axis. The following criteria are used: at a power of 22 N the needle must not be pulled out (ISO 7864 1993). Only 1 bubble is allowed in the glue and the bubble cannot be larger than 0.05 mm$^2$. For each test 20 needles were tested.

Example 1

UV curing was performed for 1, 1.2, and 1.4 seconds with a 27 G needle, A8 Hub Tritan MX711 and DYMAX 1161-M.

TABLE 2

Results

|  | 1 s UV no gamma | 1 s UV with gamma | 1.2 s UV no gamma | 1.2 s UV with gamma | 1.4 s UV no gamma | 1.4 s UV with gamma |
|---|---|---|---|---|---|---|
| MAX | 90.5 | 89.5 | 88.0 | 87.0 | 87.0 | 88.5 |
| MIN | 69.5 | 79.0 | 67.5 | 79.5 | 74.5 | 74.0 |
| average | 78.43 | 84.95 | 81.75 | 83.28 | 81.78 | 81.78 |
| σ | 5.56 | 2.87 | 4.28 | 2.46 | 3.11 | 3.87 |

As can be seen for 1 and 1.2 seconds curing, the gamma radiation significantly increases the strength of the bond between hub and needle. This enable a shorter UV radiation time.

Example 2

The test was repeated for 21 G and 27 G needles. Hub was A8 Tritan MX711, 20 needles before gamma radiation and 20 needles after gamma radiation were used. UV radiation 2 seconds, Gamma radiation 25-50 kGy. Polymer was DYMAX 1161-M.

|  | 21 G no gamma | 21 G with gamma | 27 G no gamma | 27 G with gamma |
|---|---|---|---|---|
| MAX | 191.5 | 245.0 | 92.0 | 90.5 |
| MIN | 113.0 | 160.5 | 81.5 | 76.5 |
| average | 160.68 | 206.83 | 86.03 | 84.13 |
| σ | 24.39 | 25.02 | 2.49 | 3.51 |

As can be seen, for larger needles, the effect is present also at 2 second of UV radiation.

Example 3

Acceleration Test

Acceleration conditions: needles were kept at 54° C. at 75% humidity for 29 days. Needles 21 G, 27 G, 30 G, 32 G. Hub was made of Tritan MX711, adhesive was DYMAX 1161-M. UV radiation was 2 seconds. Gamma radiation was 50 kGy.

|  | 21 G no gamma | 21 G with gamma | 21 G with gamma and acceleration | 27 G no gamma | 27 G with gamma | 27 G with gamma and acceleration |
|---|---|---|---|---|---|---|
| MAX | 179.5 | 247.0 | 243.5 | 85.5 | 90.5 | 91.5 |
| MIN | 77.0 | 211.0 | 204.5 | 66.0 | 78.5 | 79.0 |
| average | 108.38 | 228.10 | 225.13 | 77.50 | 85.08 | 85.30 |
| σ | 26.57 | 9.18 | 8.91 | 6.09 | 2.74 | 3.03 |

|  | 30 G no gamma | 30 G with gamma | 30 G with gamma and acceleration | 32 G no gamma | 32 G with gamma | 32 G with gamma and acceleration |
|---|---|---|---|---|---|---|
| MAX | 68.5 | 71.5 | 73.0 | 54.0 | 57.5 | 58.5 |
| MIN | 52.0 | 54.5 | 56.0 | 39.5 | 50.0 | 50.0 |
| average | 61.25 | 66.2 | 66.88 | 48.90 | 53.93 | 53.90 |
| σ | 4.16 | 3.79 | 4.49 | 3.59 | 2.38 | 2.35 |

As can be seen after gamma radiation, the bonding of the hub and needle is stronger than before gamma radiation, especially for larger needles. The method of combining UV radiation and gamma radiation does not deteriorate over time as the acceleration method shows.

Example 4

Test was repeated with DYMAX1193-M-SV04 and Henkel 3301 as adhesive and 27 G needle A7 hub Zeonex 690R:

|  | DYMAX1193-M-SV04 no gamma | DYMAX1193-M-SV04 with gamma | DYMAX1193-M-SV04 with gamma and acceleration | Henkel 3301 no gamma | Henkel 3301 with gamma | Henkel 3301 with gamma and acceleration |
|---|---|---|---|---|---|---|
| MAX | 92.5 | 93.5 | 89.0 | 92.5 | 93.5 | 85.0 |
| MIN | 42.0 | 65.0 | 47.0 | 38.0 | 47.0 | 22.0 |
| average | 77.0 | 84.3 | 66.6 | 77.4 | 76.4 | 50.4 |

The invention claimed is:

1. A method for using a polymer composition for connecting a first object to a second object, wherein the method comprises:
    applying a polymer composition to at least part of a surface of at least one of the first object or second object;
    connecting the first object and the second object at the surface where the polymer composition is applied and
    irradiating the polymer composition using UV-radiation over a first time period, obtaining a UV radiated polymer composition, wherein the first time period is sufficient to cure 10-90% of the polymer in the polymer composition;
    irradiating the UV radiated polymer composition with gamma-radiation over a second time period obtaining a gamma radiated polymer,
    wherein the second time period provides a gamma-radiation dosage of between 5 and 80 kGy, and wherein the gamma-radiation dosage corresponds to a sterility assurance level of at least 2 log reduction for microorganisms for the first object and the second object.

2. Method according to claim 1 wherein the first object and second object comprise plastic or metal, wherein the first object is substantially in its entirety made of plastic or metal, wherein the first and second object are of a different material.

3. Method according to claim 1, wherein the first time period is sufficient to cure 20-80% of the polymer.

4. The method according to claim 1, wherein the polymer composition is curable under the influence of visible light or UV light, or both.

5. The method according to claim 1, wherein the polymer comprises at least one monomer selected from the group consisting of isobornyl acrylate, urethane acrylate, urethane methacrylate, acrylamide, and N,N-dimethylacrylamide.

6. The method according to claim 1, wherein the polymer composition is substantially free of bisphenol-A.

7. The method according to claim 1, wherein the first and second object comprise plastic, wherein the plastic is a copolyester and the plastic is permeable for UV and/or gamma radiation.

8. The method according to claim 1, wherein the first and second object comprise metal, wherein the metal is stainless steel.

9. The method according to claim 1, wherein one of the objects is plastic and one of the objects is metal and wherein the plastic object is a hub and the metal object is a needle or cannula.

\* \* \* \* \*